United States Patent
Miura

(10) Patent No.: US 8,215,156 B2
(45) Date of Patent: Jul. 10, 2012

(54) METHOD FOR MEASURING VISCOSITY AND/OR ELASTICITY OF LIQUID

(75) Inventor: Shinsuke Miura, Tokyo (JP)

(73) Assignee: Sekonic Corporation, Tokyo (JP)

( * ) Notice: Subject to any disclaimer, the term of this patent is extended or adjusted under 35 U.S.C. 154(b) by 374 days.

(21) Appl. No.: 12/458,390

(22) Filed: Jul. 10, 2009

(65) Prior Publication Data
US 2010/0005865 A1    Jan. 14, 2010

(30) Foreign Application Priority Data

Jul. 10, 2008    (JP) .................................. 2008-180590

(51) Int. Cl.
*G01N 11/10* (2006.01)

(52) U.S. Cl. ..................... 73/54.41; 73/54.24; 73/54.25; 324/727

(58) Field of Classification Search .................. 73/54.41, 73/54.25; 324/727
See application file for complete search history.

(56) References Cited

U.S. PATENT DOCUMENTS

| 4,862,384 | A | * | 8/1989 | Bujard et al. ..................... 702/54 |
| 5,201,215 | A | * | 4/1993 | Granstaff et al. ............. 73/54.41 |
| 5,764,068 | A | * | 6/1998 | Katz et al. ..................... 324/727 |
| 6,289,734 | B1 | * | 9/2001 | Daugela .......................... 73/573 |
| 6,672,140 | B2 | * | 1/2004 | Miura .......................... 73/54.25 |

FOREIGN PATENT DOCUMENTS

| JP | 3348162 | 9/2002 |
| JP | 4083621 | 2/2008 |

\* cited by examiner

*Primary Examiner* — Hezron E Williams
*Assistant Examiner* — Hoang Nguyen
(74) *Attorney, Agent, or Firm* — Wenderoth, Lind & Ponack, L.L.P.

(57) ABSTRACT

Viscosity and elasticity of a liquid are measured by immersing and vibrating a liquid tester in the liquid to be tested and measuring three frequency values that are a resonance frequency value on an amplitude characteristic curve obtained through vibration of the liquid tester in the liquid being tested, a low frequency value lower than the resonance frequency value on the amplitude characteristic curve at a phase angle smaller than a phase angle of 90 degrees at a resonance point on a phase angle characteristic curve obtained through the vibration in the liquid being tested, and a high frequency value higher than the resonance frequency value on the amplitude characteristic curve at a phase angle larger than the phase angle at the resonance point on the phase angle characteristic curve.

8 Claims, 2 Drawing Sheets

METHOD FOR MEASURING VISCOSITY AND/OR ELASTICITY OF LIQUID

BACKGROUND OF THE INVENTION

1. Field of the Invention

The present invention relates to a method for measuring the viscosity and/or elasticity of a liquid by which the viscoelasticity of the liquid to be tested can be accurately measured, and the viscosity or elasticity can be accurately determined from the viscoelasticity.

2. Description of the Related Art

Japanese Patent Publication No. 4083621 discloses a method for measuring a viscosity value (viscosity). By this method, a vibrator (such as a piezoelectric device) is resonated in a liquid to be tested, and the viscosity value (the viscosity) of the liquid is measured from the difference between the resonance frequency and either a low frequency value (a half-value frequency f1) lower than the resonance frequency value or a high frequency value (a half-value frequency f2) higher than the resonance frequency value.

Japanese Patent Publication No. 3348162 discloses a method for measuring the viscoelasticity of a liquid. By this method, the frequency and the amplitude that are varied by the inherent viscoelasticity of the liquid are detected from the vibration of a liquid tester in the liquid to be tested. The impedance of the liquid is determined from the frequency and the amplitude, and the viscosity value and the elasticity value are determined from the real part and the imaginary part of the impedance.

By the viscosity measurement method disclosed in Japanese Patent Publication No. 4083621, however, a viscosity value is measured by determining the real part of the impedance of the subject liquid based on the difference between the resonance frequency and either the half-value frequency f1 or the half-value frequency f2. By a measurement method involving only the real part of the impedance like this method, only the real part of complex viscosity can be determined. As a result, the viscosity value of a high viscosity liquid to be tested cannot be measured with accuracy, and it is impossible to measure both the viscosity value and the elasticity value that are required for determining the dynamic characteristics of the liquid.

By a measurement method involving determination of the impedance of a liquid from the frequency and the amplitude attributable to the inherent viscoelasticity of the liquid like the method disclosed in Japanese Patent Publication No. 3348162, or by a measurement method involving the real part of the impedance as the reciprocal of a sensor output voltage proportional to the amplitude, the measurement accuracy becomes poorer, since the amplitude becomes smaller as the viscosity of the tested liquid becomes higher.

BRIEF SUMMARY OF THE INVENTION

The present invention provides a method for measuring the viscosity and/or elasticity of a liquid by which the viscoelasticity of the tested liquid can be accurately measured, and the viscosity or elasticity can be precisely determined from the viscoelasticity.

A first measurement method according to the present invention is a method for measuring the viscosity and/or elasticity of a liquid to be tested by vibrating a liquid tester immersed in the liquid to be tested with a drive source of a vibrator such as a piezoelectric device, or by immersing and vibrating the vibrator as the liquid tester in the liquid to be tested. This method includes: measuring three frequency values that are the resonance frequency value (f0) on the amplitude characteristic curve obtained through the vibration of the liquid tester in the liquid being tested, a low frequency value (f1) lower than the resonance frequency value (f0) on the amplitude characteristic curve, and a high frequency value (f2) higher than the resonance frequency value (f0) on the amplitude characteristic curve; calculating the real part of the impedance of the liquid being tested, using the high frequency value (f2) and the low frequency value (f1); calculating the imaginary part of the impedance of the liquid being tested, using the resonance frequency value (f0); and calculating the viscosity value and/or the elasticity value of the liquid being tested from the real part and the imaginary part of the impedance.

A second measurement method according to the present invention also includes: measuring three frequency values that are the resonance frequency value (f0) on the amplitude characteristic curve obtained through the vibration of the liquid tester in the liquid being tested, a low frequency value (f1) lower than the resonance frequency value (f0) on the amplitude characteristic curve, and a high frequency value (f2) higher than the resonance frequency value (f0) on the amplitude characteristic curve; calculating the real part and the imaginary part of the impedance of the liquid being tested, using the three frequency values that are the resonance frequency value (f0), the low frequency value (f1), and the high frequency value (f2); and calculating the viscosity value and/or the elasticity value of the liquid being tested from the real part and the imaginary part of the impedance.

Preferably, the low frequency value (f1) and the high frequency value (f2) represent the frequencies at symmetrical phase angles with respect to the resonance point on the phase angle characteristic curve obtained through the vibration in the liquid being tested.

By the measurement method according to the present invention, the real part and the imaginary part of impedance are determined with the use of the resonance frequency (f0), the low frequency value (f1), and the high frequency value (f2). Even if the liquid to be tested is a high viscosity liquid, the viscoelasticity of the liquid can be accurately measured, and the viscosity or elasticity can be accurately determined from the viscoelasticity.

DETAILED DESCRIPTION OF THE INVENTION

The following is a description of preferred embodiments of the present invention, with reference to FIGS. 1 through 4.

Figure 1:
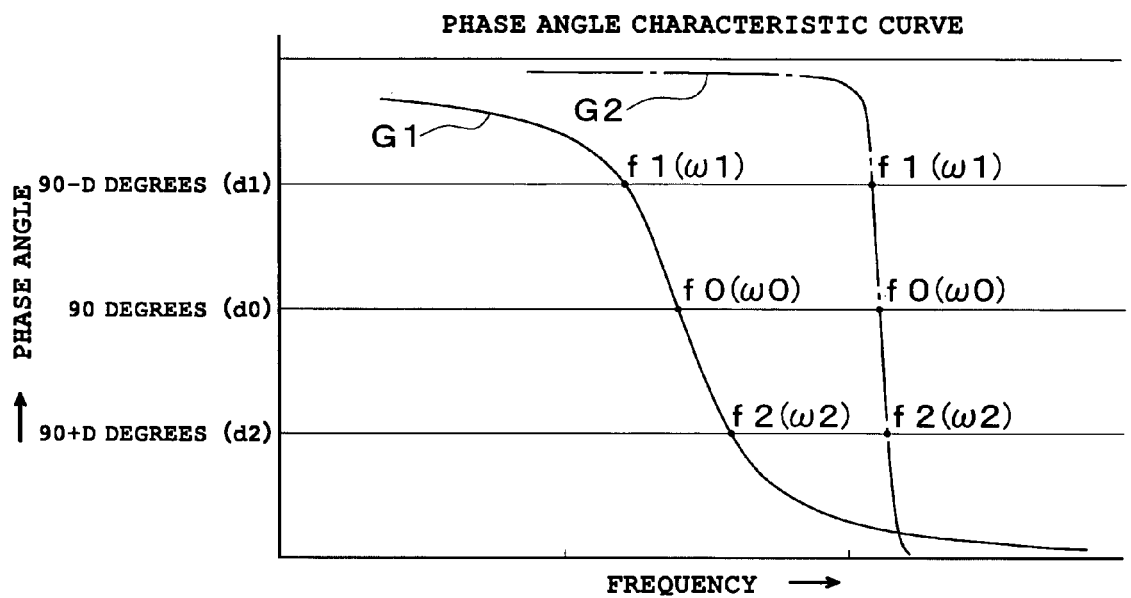
FIG. 1 shows the phase angle characteristic curves observed when a liquid tester is vibrated in a liquid to be tested.

In FIG. 1, G1 is the characteristic curve of the delay angle of the amplitude with respect to the vibrational frequency of a liquid tester 1 that vibrates in a liquid to be tested, or the characteristic curve of the phase angle.

On the other hand, G2 is the characteristic curve of the delay angle of the amplitude with respect to the vibrational frequency observed when the liquid tester 1 is vibrated in the air, or the characteristic curve of the phase angle.

Figure 2:
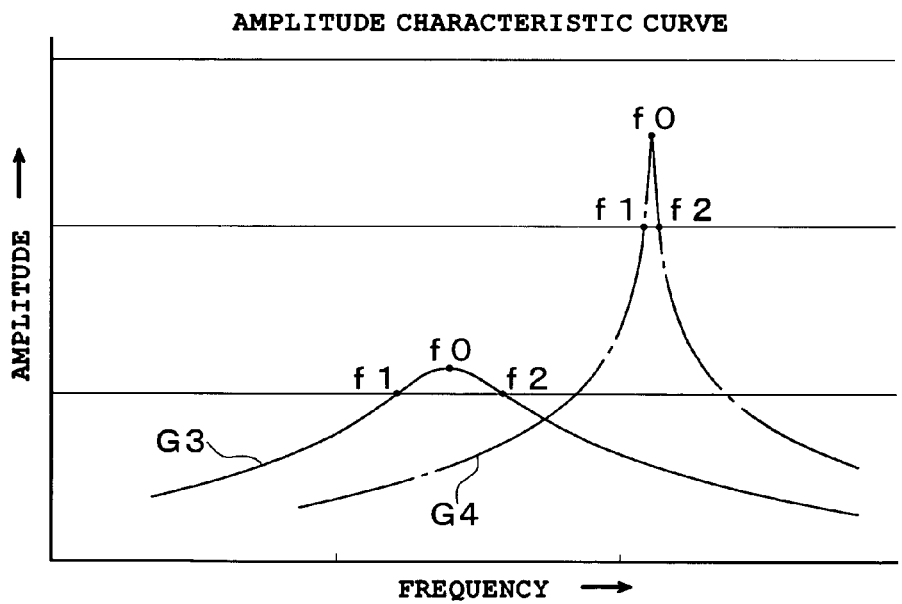
FIG. 2 shows the amplitude characteristic curves observed when the liquid tester is vibrated in the liquid to be tested.

In FIG. 2, G3 is the characteristic curve of the amplitude with respect to the vibrational frequency of the liquid tester 1 that vibrates in the liquid to be tested.

On the other hand, G4 is the characteristic curve of the amplitude with respect to the vibrational frequency observed when the liquid tester 1 is vibrated in the air.

In FIG. 1, f0, f1, and f2 on the phase angle characteristic curves G1 and G2 represent the frequencies at the respective phase angles of 90 degrees, 90−d degrees, and 90+d degrees. In this case, f0 represents the resonance frequency, f1 represents a frequency lower than the resonance frequency, and f2 represents a frequency higher than the resonance frequency.

Here, −d is the angle to be subtracted from 90 degrees, and +d is the angle to be added to 90 degrees. For example, d represents an angle of 45 degrees of symmetric point with respect to 90 degrees, and in this case, 90−d degrees is 45 degrees, and 90+d degrees is 135 degrees.

In this embodiment, f1 and f2 are used as example frequencies at symmetrical phase angles with respect to the resonance point existing on the phase angle characteristic curves obtained through vibrations of the liquid to be tested.

Meanwhile, f0, f1, and f2 on the amplitude characteristic curves G3 and G4 in FIG. 2 represent the frequencies on the amplitude characteristic curves equivalent to f0, f1, and f2 on the phase angle characteristic curves G1 and G2. Here, f0 represents the resonance frequency, f1 represents a frequency lower than the resonance frequency, and f2 represents a frequency higher than the resonance frequency.

Figure 4:
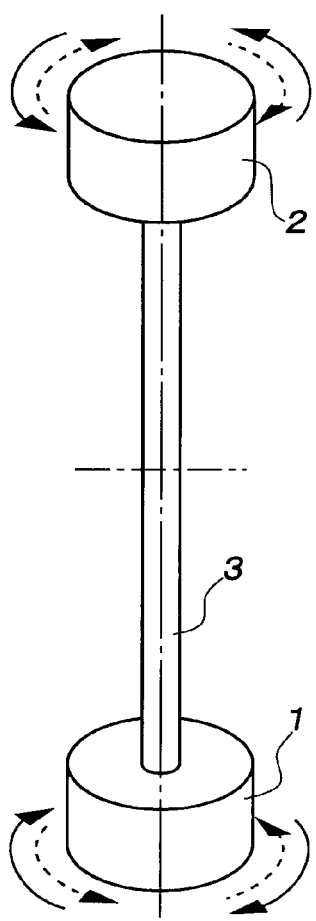
FIG. 4 is a perspective view showing a vibrator device that vibrates the liquid tester with a drive source provided outside the tested liquid, and the vibration mode for the liquid tester.

A vibrator device including the liquid tester 1 in accordance with the present invention is either a device that vibrates (or resonates) the liquid tester 1 by transmitting the vibration of a drive source 2 formed with a piezoelectric device or an electromagnetic drive device to be driven outside the tested liquid via a vibration transmitting shaft 3 as shown in FIG. 4, or a device that vibrates the liquid tester 1 that is a vibrator formed with a piezoelectric device immersed in the liquid to be tested as disclosed in Japanese Patent Publication No. 4083621.

Figure 3A:
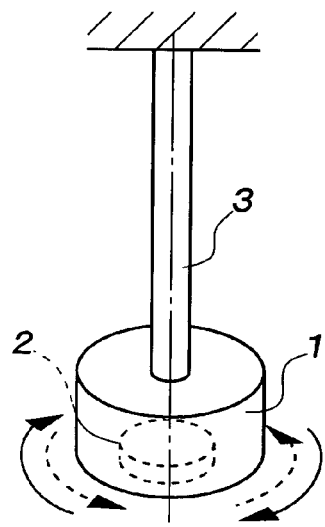
FIGS. 3A and 3B are perspective views showing the vibration modes for the liquid tester in vibrator devices that include a drive source in the liquid tester immersed in the liquid to be tested.
Figure 3B:
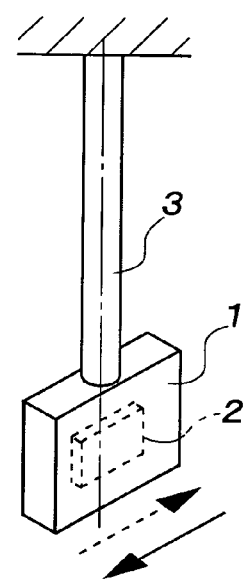

The vibrator device may also be a device that includes the drive source 2 formed with a piezoelectric device in the liquid tester 1, and vibrates the liquid tester 1 in the liquid to be tested, as shown in FIGS. 3A and 3B.

Examples vibration modes for the liquid tester 1 include the mode for vibrating the liquid tester 1 in a circle direction about the shaft line as shown in FIG. 3A, and the mode for vibrating the liquid tester 1 in a transverse direction in the liquid to be tested as shown in FIG. 3B.

The present invention relates to a method for measuring the viscosity value and/or elasticity value of a liquid to be tested by immersing the liquid tester 1 that is vibrated by a vibrator in the liquid to be tested, as described above. By a first measurement method according to the present invention, the three frequency values, which are the resonance frequency value f0 on the phase angle characteristic curve (G1 in FIG. 1) and the amplitude characteristic curve (G3 in FIG. 2) obtained through the vibration of the liquid tester 1 in the liquid to be tested, the low frequency value f1 lower than the resonance frequency value f0 on the amplitude characteristic curve, and the high frequency value f2 higher than the resonance frequency value f0 on the amplitude characteristic curve, are first measured. The real part of the impedance of the tested liquid is calculated with the use of the high frequency value f2 and the low frequency value f1, and the imaginary part of the impedance of the tested liquid is calculated with the use of the resonance frequency value f0. The viscosity value and/or elasticity value of the tested liquid are then calculated from the real part and imaginary part of the impedance.

By a second measurement method according to the present invention, the three frequency values, which are the resonance frequency value f0 on the amplitude characteristic curve obtained through the vibration of the liquid tester 1 in the liquid to be tested, the low frequency value f1 lower than the resonance frequency value f0 on the amplitude characteristic curve, and the high frequency value f2 higher than the resonance frequency value f0 on the amplitude characteristic curve, are first measured. The real part and imaginary part of the impedance of the tested liquid are calculated with the use of the three frequency values: the resonance frequency value f0, the low frequency value f1, and the high frequency value f2. The viscosity value and/or elasticity value of the tested liquid are then calculated from the real part and imaginary part of the impedance.

It is preferable that the low frequency value f1 and the high frequency value f2 are the frequencies at phase angles located at the symmetrical points with respect to the resonance point on the phase angle characteristic curve G1 obtained through the vibration in the tested liquid.

In other words, the low frequency value f1 and the high frequency value f2 are the frequencies at the symmetrical points located at the same amplitude level with respect to the resonance point on the amplitude characteristic curve G3 obtained through the vibration in the tested liquid.

As can be seen from the comparison between the phase angle characteristic curves G1 and G2 in FIG. 1, and the comparison between the amplitude characteristic curves G3 and G4 in FIG. 2, the resonance frequency value f0 in the tested liquid is lower than the resonance frequency value f0 in the air, and the difference between the high frequency value f2 and the low frequency value f1 in the tested liquid is larger than the difference between the high frequency value f2 and the low frequency value f1 in the air.

In other words, as the viscosity of the tested liquid becomes greater, the resonance frequency value f0 shift to the lower frequency side, and the difference between the high frequency value f2 and the low frequency value f1 becomes greater.

The following is a more detailed description of the first and second methods for measuring the viscosity and/or elasticity of a liquid in accordance with the present invention, with reference to equations (1) through (47).

The delays in the vibration amplitude with respect to a drive signal are represented by phase angles d0, d1, and d2. As f0 represents the resonance point, d0 is 90 degrees. At f1 and f2, d1 is 90−d degrees, d2 is 90+d degrees, and the angular frequencies of f0, f1, and f2 are represented by $\omega_0$, $\omega_1$, and $\omega_2$. Here, $\omega$ is equal to $2\pi f$.

The angular frequencies at f0, f1, and f2 in the air are represented by $\omega_{00}$, $\omega_{01}$, and $\omega_{02}$, respectively. Here, $\omega_{00}$, $\omega_{01}$, and $\omega_{02}$ are inherent values of the vibrator devices shown in FIGS. 3A, 3B, and 4, and are constants that are measured in advance and are stored in a memory of a processor provided in each of the vibrator devices. The processor has calculating functions.

The liquid tester 1 vibrates a liquid having viscosity $\eta$ and density $\rho$ at the resonance angular frequency $\omega_0$ of the liquid tester 1. The ratio F/v between the vibration velocity v of the tested liquid and the resistive force F generated from the tested liquid is called the impedance Z of the tested liquid.

The vibration velocity v of the waves propagated to the tested liquid can be determined as the solution of a wave equation. The impedance Z of the tested liquid is determined according to the following equation (1) based on the vibration velocity v determined by plane wave approximation. Here, S represents a constant proportional to the surface area of the liquid tester 1, and j represents the symbol of an imaginary part.

$$Z = S \cdot \sqrt{j\omega \cdot \rho \cdot \eta} \qquad \text{Equation (1):}$$

Where the equation (1) is Maclaurin-expanded in the vicinity of $\omega_0$ so as to express the impedance Z with $\omega_0$, the impedance Z of the tested liquid can be expressed by the following equation (2) when $\omega_2$ is very close to $\omega_0$.

$$Z = S \cdot \sqrt{j\omega_0 \cdot \rho \cdot \eta} \qquad \text{Equation (2):}$$

When $\omega_1$ and $\omega_2$ greatly differ from $\omega_0$, the impedance Z of the tested liquid is expressed by the following equation (3). Here, $\omega$ is $\omega_0$, $\omega_1$, or $\omega_2$.

$$Z = S \cdot \sqrt{j\omega_0 \cdot \rho \cdot \eta} \cdot \frac{\omega + \omega_0}{2 \cdot \omega_0} \qquad \text{Equation (3)}$$

If the tested liquid is a viscoelastic material, the viscosity $\eta$ of the tested liquid is a complex number, and can be expressed by the following equation (4).

$$\eta = \eta' - j \cdot \eta'' \qquad \text{Equation (4)}$$
$$= \sqrt{\eta'^2 + \eta''^2} \cdot e^{-j\delta}$$

The phase angle $\delta$ of the complex viscosity is defined like the equation (5).

$$\tan\delta = \frac{\eta''}{\eta'} \qquad \text{Equation (5)}$$

The absolute value $\eta_1$ of the complex viscosity is defined like the equation (6).

$$\sqrt{\eta'^2 + \eta''^2} \eta_1 \qquad \text{Equation (6):}$$

The equation (4) can be expressed by the equation (7) using $\eta_1$.

$$\eta = \eta_1 \cdot e^{-j\delta} \qquad \text{Equation (7):}$$

The equations (1) through (7) are common between the first and second methods for measuring the viscosity and/or elasticity of a liquid. In the following, the calculations of the real part R and the imaginary part X of the impedance Z according to the first measurement method are described with the use of equations (8) through (29).

When $\omega_1$ and $\omega_2$ are very close to $\omega_0$, or when the impedance Z of the tested liquid is almost the same at the three measurement values, the impedance Z is determined by assigning the equation (7) to the equation (2), and is expressed by the following equations (8) and (9).

$$Z = S \cdot \sqrt{j\omega_0 \cdot \rho \cdot \eta_l \cdot e^{-j\delta}} \qquad \text{Equation (8)}$$
$$= S \cdot \sqrt{\omega_0 \cdot \rho \cdot \eta_l} \cdot \cos\left(\frac{\pi}{4} - \frac{\delta}{2}\right) + \qquad \text{Equation (9)}$$

-continued
$$j \cdot S \cdot \sqrt{\omega_0 \cdot \rho \cdot \eta_l} \cdot \sin\left(\frac{\pi}{4} - \frac{\delta}{2}\right)$$

Where the real part R and the imaginary part X of the impedance Z are defined by the equations (10) and (11), the impedance Z can be expressed by the equation (12).

$$R = S \cdot \sqrt{\omega_0 \cdot \rho \cdot \eta_l} \cdot \cos\left(\frac{\pi}{4} - \frac{\delta}{2}\right) \qquad \text{Equation (10)}$$

$$X = S \cdot \sqrt{\omega_0 \cdot \rho \cdot \eta_l} \cdot \sin\left(\frac{\pi}{4} - \frac{\delta}{2}\right) \qquad \text{Equation (11)}$$

$$Z = R + j \cdot X \qquad \text{Equation (12)}$$

The inertia moment of the liquid tester 1 is represented by M, the torsion spring constant is represented by K, and the internal resistance of the torsion spring constant is represented by r.

When the liquid tester 1 is driven by a drive force $F = F_0 \cdot e^{j\omega t}$ in the air, the displacement of the liquid tester 1 is $\chi = \chi_0 \cdot e^{j\omega t}$. The displacement can be expressed by the vibration equation according to the following equation (13).

$$-\omega^2 \cdot M \cdot x_0 + j \cdot \omega \cdot r \cdot x_0 + K \cdot x_0 = F_0 \qquad \text{Equation (13):}$$

When the liquid tester 1 is immersed in the tested liquid, the real part R and the imaginary part X of the impedance Z of the tested liquid respectively act as an addition to the resistance and an addition to the inertia moment in the vibrator device.

Accordingly, the internal resistance r and the inertia moment M become r+R and M+X/$\omega$, respectively, and the equation (13) turns into the following equation (14).

$$-\omega^2 \cdot \left(M + \frac{X}{\omega}\right) \cdot x_0 + j \cdot \omega \cdot (r + R) \cdot x_0 + K \cdot x_0 = F_0 \qquad \text{Equation (14)}$$

By transforming the equation (14), the transmission function $\chi_0/F_0$ with respect to the drive force F of the movement of the liquid tester 1 can be expressed by the equation (15).

$$\frac{x_0}{F_0} = \frac{1}{-\omega^2 \cdot \left(M + \frac{X}{\omega}\right) + K + j \cdot \omega \cdot (r + R)} \qquad \text{Equation (15)}$$

With $\omega_{00}^2$ being equal to K/M, the denominator of the equation (15) is rationalized to find the equation (16).

$$\frac{x_0}{F_0} = \frac{1}{M} \cdot \frac{1}{\omega_{00}^2 - \omega^2 \cdot \left(1 + \frac{X}{\omega \cdot M}\right) + j \cdot \omega \cdot \frac{r+R}{M}} \qquad \text{Equation (16)}$$
$$= \frac{1}{M} \cdot \frac{\omega_{00}^2 - \omega^2 \cdot \left(1 + \frac{X}{\omega \cdot M}\right) - j \cdot \omega \cdot \frac{r+R}{M}}{\left\{\omega_{00}^2 - \omega^2 \cdot \left(1 + \frac{X}{\omega \cdot M}\right)\right\}^2 + \left(\omega \cdot \frac{r+R}{M}\right)^2},$$

Where D represents the phase angle indicating the delay of the movement of the liquid tester 1 with respect to the drive force, tan D is expressed by the equation (17).

$$\tan D = \frac{\omega \cdot \frac{r+R}{M}}{\omega_{00}^2 - \omega^2 \cdot \left(1 + \frac{X}{\omega \cdot M}\right)} \qquad \text{Equation (17)}$$

Here, D represents the phase angles at the three points $d_1$, $d_2$, and $d_0$ on the phase angle characteristic curves shown in FIG. 1. Since the angular frequencies at these three points are $\omega_1$, $\omega_2$, and $\omega_0$, the three equations formed with the three sets $(d_1, \omega_1)$, $(d_2, \omega_2)$, and $(d_0, \omega_0)$ are the following equations (18), (19), and (20).

$$\tan d_1 = \frac{\omega_1 \cdot \frac{r+R}{M}}{\omega_{00}^2 - \omega_1^2 \cdot \left(1 + \frac{X}{\omega_1 \cdot M}\right)} \qquad \text{Equation (18)}$$

$$\tan d_2 = \frac{\omega_2 \cdot \frac{r+R}{M}}{\omega_{00}^2 - \omega_2^2 \cdot \left(1 + \frac{X}{\omega_2 \cdot M}\right)} \qquad \text{Equation (19)}$$

$$\omega_{00}^2 - \omega_0^2 \cdot \left(1 + \frac{X}{\omega_0 \cdot M}\right) = 0 \qquad \text{Equation (20)}$$

Since $d_1$ is 90−d, and $d_2$ is 90+d, $\tan d_1$ is equal to cot d, and $\tan d_2$ is equal to −cot d. Here, cot d is 1/C. With the use of C, the equations (18), (19), and (20) are transformed into the following equations (21), (22), and (23).

$$\omega_{00}^2 - \omega_1^2 - \frac{X}{M} \cdot \omega_1 = C \cdot \omega_1 \cdot \frac{r+R}{M} \qquad \text{Equation (21)}$$

$$\omega_{00}^2 - \omega_2^2 - \frac{X}{M} \cdot \omega_2 = -C \cdot \omega_2 \cdot \frac{r+R}{M} \qquad \text{Equation (22)}$$

$$\omega_{00}^2 - \omega_0^2 - \frac{X}{M} \cdot \omega_0 = 0 \qquad \text{Equation (23)}$$

The following equation (24) is obtained from the equations (21) and (22).

$$\omega_{00}^2 \cdot (\omega_2 - \omega_1) - (\omega_1^2 \cdot \omega_2 - \omega_1 \cdot \omega_2^2) = 2 \cdot C \cdot \omega_1 \cdot \omega_2 \cdot \frac{r+R}{M} \qquad \text{Equation (24)}$$

The following equation (25) expressing r+R/M is determined from the equation (24).

$$\frac{r+R}{M} = \frac{(\omega_2 - \omega_1) \cdot (\omega_{00}^2 + \omega_1 \cdot \omega_2)}{2 \cdot C \cdot \omega_1 \cdot \omega_2} \qquad \text{Equation (25)}$$

Also, the equation (26) expressing X/M is determined from the equation (23).

$$\frac{X}{M} = \frac{\omega_{00}^2 - \omega_0^2}{\omega_0} \qquad \text{Equation (26)}$$

In the air, $\omega_1$, $\omega_2$, and $\omega_0$ are the known constants $\omega_{01}$, $\omega_{02}$, and $\omega_{00}$, and are stored in the memory of the processor for processing signals obtained form the vibrator device.

Since R is 0, and X is 0 in the air, the equation (25) is transformed into the following equation (27).

$$\frac{r}{M} = \frac{(\omega_{02} - \omega_{01}) \cdot (\omega_{00}^2 + \omega_{01} \cdot \omega_{02})}{2 \cdot C \cdot \omega_{01} \cdot \omega_{02}} \qquad \text{Equation (27)}$$

As is apparent from the equation (27), r/M is a known constant. With the use of r/M of the equation (27), the real part R and the imaginary part X can be determined according to the following equations (28) and (29).

$$R = \frac{M}{2 \cdot C} \cdot \frac{(\omega_2 - \omega_1) \cdot (\omega_{00}^2 + \omega_1 \cdot \omega_2)}{\omega_1 \cdot \omega_2} - r \qquad \text{Equation (28)}$$

$$X = M \cdot \frac{(\omega_{00} - \omega_0) \cdot (\omega_{00} + \omega_0)}{\omega_0} \qquad \text{Equation (29)}$$

Next, the calculations of the real part R and the imaginary part X of the impedance Z according to the second measurement method are described with the use of equations (30) through (33).

When $\omega_1$ and $\omega_2$ greatly differ from $\omega_0$, the impedance Z of the tested liquid is expressed by the equation (3). Since the internal resistance r of the device is considered to be small enough to ignore, the equations (21) and (22) are transformed into the following equations (30) and (31).

$$\omega_{00}^2 - \omega_1^2 - \frac{X}{M} \cdot \omega_1 \cdot \frac{\omega_1 + \omega_0}{2 \cdot \omega_0} = C \cdot \omega_1 \cdot \frac{\omega_1 + \omega_0}{2 \cdot \omega_0} \cdot \frac{R}{M} \qquad \text{Equation (30)}$$

$$\omega_{00}^2 - \omega_2^2 - \frac{X}{M} \cdot \omega_2 \cdot \frac{\omega_2 + \omega_0}{2 \cdot \omega_0} = -C \cdot \omega_2 \cdot \frac{\omega_2 + \omega_0}{2 \cdot \omega_0} \cdot \frac{R}{M} \qquad \text{Equation (31)}$$

According to the equations (30) and (31), the real part R and the imaginary part X are expressed by the following equations (32) and (33).

$$R = M \cdot \frac{\omega_{00} \cdot (\omega_2 - \omega_1) \cdot \{\omega_{00}^2 + \omega_1 \cdot \omega_2 + \omega_0 \cdot (\omega_1 + \omega_2)\}}{C \cdot \omega_1 \cdot \omega_2 \cdot (\omega_1 + \omega_2) \cdot (\omega_2 + \omega_0)} \qquad \text{Equation (32)}$$

$$X = M \cdot \frac{\omega_{00}^2 \cdot (\omega_1 + \omega_2) + 2 \cdot \omega_{00}^2 \cdot \omega_0 - \omega_1 \cdot \omega_2 \cdot (\omega_1 + \omega_2) - \omega_0^2 \cdot (\omega_1^2 + \omega_2^2)}{C \cdot \omega_1 \cdot \omega_2 \cdot (\omega_1 + \omega_2) \cdot (\omega_2 + \omega_0)} \qquad \text{Equation (33)}$$

As described above, by the first measurement method, the liquid tester 1 is vibrated in the tested liquid, and the three angular frequencies $\omega_1$, $\omega_2$, and $\omega_0$ at the three phase differences $d_1$, $d_2$, and $d_0$ are measured. The real part R of the impedance Z of the tested liquid is calculated by the processor according to the equation (28) using the high frequency value f2 and the low frequency value f1. The imaginary part X of the impedance Z of the tested liquid is calculated according to the equation (29) using the resonance frequency value f0.

By the second measurement method, the real part R and the imaginary part X of the impedance Z of the tested liquid are calculated according to the equations (32) and (33) using the high frequency value f2, the low frequency value f1, and the resonance frequency value f0.

Next, the first measurement method for measuring the viscosity and/or elasticity of the liquid based on the real part R and the imaginary part X determined according to the equations (28) and (29) is described with the use of equations (34) through (40).

Based on the equations (10) and (11), the phase angle δ of the complex viscosity is calculated according to the following equation (34).

$$\delta = \frac{\pi}{2} - 2 \cdot \arctan\left(\frac{X}{R}\right) \quad \text{Equation (34)}$$

Since $R^2+X^2=S^2 \cdot \omega_0 \cdot \rho \cdot \eta_1$ according to the equations (10) and (11), the absolute value $\eta_1$ of the complex viscosity is calculated according to the following equation (35) using R and X determined by the equations (28) and (29).

$$\eta_l = \frac{R^2 + X^2}{S^2 \cdot \omega_0 \cdot \rho} \quad \text{Equation (35)}$$

Based on the phase angle δ of the complex viscosity determined by the equation (34) and the absolute value $\eta_1$ of the complex viscosity determined by the equation (35), the complex viscosity η is calculated according to the following equation (36).

$$\eta = \eta_l \cdot e^{-j\delta} \quad \text{Equation (36)}$$
$$= \eta_l \cdot \cos\delta - j \cdot \eta_l \cdot \sin\delta$$
$$= \eta' - j \cdot \eta''$$
$$= n' - j \cdot \frac{G'}{\omega_0}$$

Based on the equation (36), the real part η' of the complex viscosity η is calculated according to the following equation (37).

$$\eta' = \eta_1 \cdot \cos\delta \quad \text{Equation (37):}$$

The imaginary part η" of the complex viscosity η is calculated according to the following equation (38).

$$\eta'' = \eta_1 \cdot \sin\delta \quad \text{Equation (38):}$$

The real part G' of the complex elastic modulus G is calculated according to the following equation (39).

$$G' = \omega_0 \cdot \eta_1 \cdot \sin\delta \quad \text{Equation (39):}$$

The imaginary part G" of the complex elastic modulus G is calculated according to the following equation (40).

$$G'' = \omega_0 \cdot \eta_1 \cdot \cos\delta \quad \text{Equation (40):}$$

Next, the second measurement method for measuring the viscosity and/or elasticity of the liquid based on the real part R and the imaginary part X determined according to the equations (32) and (33) is described with the use of equations (41) through (47).

Even where the impedance Z is expressed by the equation (3), the real part R and the imaginary part X of the impedance Z at the resonance frequency value are expressed by the equations (10) and (11). Based on the equations (10) and (11), the phase angle δ of the complex viscosity is calculated according to the following equation (41).

$$\delta = \frac{\pi}{2} - 2 \cdot \arctan\left(\frac{X}{R}\right). \quad \text{Equation (41)}$$

Since $R^2+X^2=S^2 \cdot \omega_0 \cdot \rho \cdot \eta_1$ according to the equations (10) and (11), the absolute value $\eta_1$ of the complex viscosity is calculated according to the following equation (42) using R and X determined by the equations (32) and (33).

$$\eta_l = \frac{R^2 + X^2}{S^2 \cdot \omega_0 \cdot \rho} \quad \text{Equation (42)}$$

Based on the phase angle δ of the complex viscosity determined by the equation (41) and the absolute value $\eta_1$ of the complex viscosity determined by the equation (42), the complex viscosity η is calculated according to the following equation (43).

$$\eta = \eta_l \cdot e^{-j\delta} \quad \text{Equation (43)}$$
$$= \eta_l \cdot \cos\delta - j \cdot \eta_l \cdot \sin\delta$$
$$= \eta' - j \cdot \eta''$$
$$= n' - j \cdot \frac{G'}{\omega_0}$$

Based on the equation (43), the real part η' of the complex viscosity η is calculated according to the following equation (44).

$$\eta' = \eta_1 \cdot \cos\delta \quad \text{Equation (44):}$$

The imaginary part η" of the complex viscosity η is calculated according to the following equation (45).

$$\eta'' = \eta_1 \cdot \sin\delta \quad \text{Equation (45):}$$

The real part G' of the complex elastic modulus G is calculated according to the following equation (46).

$$G' = \omega_0 \cdot \eta_1 \cdot \sin\delta \quad \text{Equation (46):}$$

The imaginary part G" of the complex elastic modulus G is calculated according to the following equation (47).

$$G'' = \omega_0 \cdot \eta_1 \cdot \cos\delta \quad \text{Equation (47):}$$

As described above, by the first measurement method, the three frequency values, which are the resonance frequency value f0 on the phase angle characteristic curve (G1 in FIG. 1) and the amplitude characteristic curve (G3 in FIG. 2) obtained through vibration of the liquid tester 1 in a liquid to be tested, the low frequency value f1 lower than the resonance frequency value f0 on the amplitude characteristic curve, and the high frequency value f2 higher than the resonance frequency value f0 on the amplitude characteristic curve, are first measured. The real part of the impedance of the tested liquid is calculated with the use of the high frequency value f2 and the low frequency value f1, and the imaginary part of the impedance of the tested liquid is calculated with the use of the resonance frequency value f0. The viscosity value and/or the elasticity value of the tested liquid are calculated from the real part and imaginary part of the impedance. By the second measurement method, the three frequency values, which are the resonance frequency value f0 on the amplitude characteristic curve obtained through vibration of the liquid tester 1 in a liquid to be tested, the low frequency value f1 lower than the resonance frequency value f0 on the amplitude characteristic curve, and the high frequency value f2 higher than the resonance frequency value f0 on the amplitude characteristic curve, are first measured. The real part and the imaginary part of the impedance of the tested liquid are calculated with the use of the three frequency values, which are the resonance frequency value f0, the low frequency value f1, and the high frequency value f2. The viscosity value and/or the elasticity value of the tested liquid are calculated from the real part and imaginary part of the impedance. By the first and second measurement methods, accurate viscoelasticity measurement can be performed on a wide variety of liquids ranging from low viscosity liquids to high viscosity liquids to be tested. Furthermore, viscosity or elasticity can be accurately determined from the viscoelasticity.

Accordingly, it is possible to effectively solve the problems of the conventional methods, such as the problem that the real part and the imaginary part of complex viscosity cannot be determined, and therefore the viscosity value of a high viscoelasticity liquid to be tested cannot be accurately measured as in a case where only the real part of the impedance is used as disclosed in Japanese Patent Publication No. 4083621, and the problem that it is impossible to measure both the viscosity value and the elasticity value required for determining the dynamic characteristics of the liquid.

Also, it is possible to effectively solve the problems of the conventional methods, such as the problem that the amplitude becomes smaller as the viscosity of the tested liquid becomes higher, and therefore the measurement accuracy becomes poorer, as in a case where the impedance of the liquid is determined from the frequency and amplitude attributable to the inherent viscoelasticity of the liquid, or where the real part of the impedance is regarded as the reciprocal of the sensor output voltage proportional to the amplitude as disclosed in Japanese Patent Publication No. 3348162.

What is claimed is:

1. A method for measuring viscosity and elasticity of a liquid by immersing and vibrating a liquid tester in the liquid to be tested, the method comprising:
    measuring three frequency values that are a resonance frequency value (f0) on an amplitude characteristic curve obtained through vibration of the liquid tester in the liquid being tested, a low frequency value (f1) lower than the resonance frequency value (f0) on the amplitude characteristic curve at a phase angle smaller than a phase angle of 90 degrees at a resonance point on a phase angle characteristic curve obtained through the vibration in the liquid being tested, and a high frequency value (f2) higher than the resonance frequency value (f0) on the amplitude characteristic curve at a phase angle larger than the phase angle at the resonance point on the phase angle characteristic curve;
    calculating a real part of impedance of the liquid being tested using the high frequency value (f2) and the low frequency value (f1);
    calculating an imaginary part of the impedance of the liquid being tested using the resonance frequency value (f0); and
    calculating the viscosity value and the elasticity value of the liquid being tested from the real part and the imaginary part of the impedance.

2. A method for measuring viscosity and elasticity of a liquid by immersing and vibrating a liquid tester in the liquid to be tested, the method comprising:
    measuring three frequency values that are a resonance frequency value (f0) on an amplitude characteristic curve obtained through vibration of the liquid tester in the liquid being tested, a low frequency value (f1) lower than the resonance frequency value (f0) on the amplitude characteristic curve at a phase angle smaller than a phase angle of 90 degrees at a resonance point on a phase angle characteristic curve obtained through the vibration in the liquid being tested, and a high frequency value (f2) higher than the resonance frequency value (f0) on the amplitude characteristic curve at a phase angle larger than the phase angle at the resonance point on the phase angle characteristic curve;
    calculating a real part and an imaginary part of impedance of the liquid being tested using the three frequency values that are the resonance frequency value (f0), the low frequency value (f1), and the high frequency value (f2); and
    calculating the viscosity value and the elasticity value of the liquid being tested from the real part and the imaginary part of the impedance.

3. The method of claim 1, wherein the low frequency value (f1) and the high frequency value (f2) represent frequencies at symmetrical phase angles with respect to a resonance point on the phase angle characteristic curve obtained through the vibration in the liquid being tested.

4. The method of claim 2, wherein the low frequency value (f1) and the high frequency value (f2) represent frequencies at symmetrical phase angles with respect to a resonance point on the phase angle characteristic curve obtained through the vibration in the liquid being tested.

5. The method of claim 1, further comprising:
    immersing the liquid tester in the liquid; and
    vibrating the liquid tester in the liquid.

6. The method of claim 5, wherein the low frequency value (f1) and the high frequency value (f2) represent frequencies at symmetrical phase angles with respect to a resonance point on the phase angle characteristic curve obtained through the vibration in the liquid being tested.

7. The method of claim 2, further comprising:
    immersing the liquid tester in the liquid; and
    vibrating the liquid tester in the liquid.

8. The method of claim 6, wherein the low frequency value (f1) and the high frequency value (f2) represent frequencies at symmetrical phase angles with respect to a resonance point on the phase angle characteristic curve obtained through the vibration in the liquid being tested.

* * * * *